(12) United States Patent
Ehbets et al.

(10) Patent No.: US 10,001,411 B2
(45) Date of Patent: Jun. 19, 2018

(54) SPARKLE MEASUREMENT

(71) Applicant: X-Rite Switzerland GmbH, Regensdorf (CH)

(72) Inventors: Peter Ehbets, Zurich (CH); Guido Niederer, Zurich (CH)

(73) Assignee: X-Rite Switzerland GMBH, Regensdorf (CH)

( * ) Notice: Subject to any disclaimer, the term of this patent is extended or adjusted under 35 U.S.C. 154(b) by 0 days. days.

(21) Appl. No.: 15/131,832

(22) Filed: Apr. 18, 2016

(65) Prior Publication Data

US 2017/0176254 A1 Jun. 22, 2017

(30) Foreign Application Priority Data

Dec. 22, 2015 (EP) .................................. 15202161

(51) Int. Cl.
*G01J 3/02* (2006.01)
*G01J 3/45* (2006.01)
(Continued)

(52) U.S. Cl.
CPC ............... *G01J 3/2823* (2013.01); *G01J 3/51* (2013.01); *G01J 2003/2826* (2013.01)

(58) Field of Classification Search
CPC ..... G01J 3/51; G01J 3/2823; G01J 2003/2826
See application file for complete search history.

(56) References Cited

U.S. PATENT DOCUMENTS 5,963,332 A 10/1999 Feldman
6,034,372 A 3/2000 Levan
(Continued)

FOREIGN PATENT DOCUMENTS

EP 1 213 569 A2 6/2002
EP 2 551 663 A2 1/2013
(Continued)

OTHER PUBLICATIONS

A. Ferrero, J. Campos, A. M. Rabal and A. Pons "A single analytical model for sparkle and graininess patterns in texture of effect coatings" Nov. 4, 2013 | vol. 21, No. 22 | DOI:10.1364/OE.21.026812 | Optics Express 26812.*

(Continued)

*Primary Examiner* — Dominic J Bologna
(74) *Attorney, Agent, or Firm* — Hahn Loeser & Parks, LLP.

(57) ABSTRACT

A device for radiometrically gauging the surface of a measurement object (O) includes: at least one measurement array featuring an illumination array and a pick-up array; and a processor (P) for controlling the illumination array and the pick-up array and for processing measurement signals produced by the pick-up array and for providing processed image data. The illumination array exposes a region of the measurement object (O) to illumination light at an illumination angle ($\theta_i$) and an illumination aperture angle ($\alpha_i$), and the pick-up array captures measurement light, reflected by the measurement object (O), at a pick-up angle ($\theta_v$) and a pick-up aperture angle ($\alpha_v$) and guides it onto an image sensor exhibiting a pixel structure. The measurement object (O) is gauged multispectrally in multiple wavelength ranges, wherein the image sensor produces multispectral image data. Angular and spatial conditions are indicated which optimise the measurement device (MD) with regard to characterising sparkles.

13 Claims, 9 Drawing Sheets

(51) Int. Cl.
*G01J 3/28* (2006.01)
*G01J 3/51* (2006.01)

(56) References Cited

U.S. PATENT DOCUMENTS

| | | | |
|---|---|---|---|
| 2002/0122192 A1* | 9/2002 | Ott | G01J 3/02 358/1.9 |
| 2002/0167669 A1 | 11/2002 | Schwarz | |
| 2005/0286053 A1 | 12/2005 | Imura | |
| 2007/0023663 A1* | 2/2007 | Chen | G01J 3/02 250/339.02 |
| 2013/0027545 A1* | 1/2013 | Schwarz | G01N 21/474 348/135 |
| 2013/0050540 A1 | 2/2013 | Kano | |
| 2014/0152990 A1* | 6/2014 | Ehbets | G01J 3/50 356/405 |
| 2015/0260647 A1* | 9/2015 | Seto | G01N 21/55 356/445 |
| 2016/0216194 A1* | 7/2016 | Mueller | G01N 21/4738 |

FOREIGN PATENT DOCUMENTS

| | | |
|---|---|---|
| EP | 2 728 342 A1 | 5/2014 |
| WO | WO 2007/018616 A1 | 2/2007 |
| WO | WO 2015/014748 A1 | 2/2015 |

OTHER PUBLICATIONS

European Search Report (English Translation included), dated Oct. 18, 2016, Appln. No. 15202161.4.

Eric Kirchner, Werner Cramer, Making Sense of Measurement Geometries for Multi-angle Spectrophotometers, Color Research & Application, vol. 37, No. 3 (Jul. 13, 2011) XP055217548.

Kirchner, et al. "Observation of Visual Texture of Metallic and Pearlescent Materials" Color research and application, Akzo Nobel Car Refinishes, Technology Center Colorimetry, Netherlands, Aug. 31, 2006, pp. 256-266.

Kirchner, et al. "Visibility of Sparkle in Metallic Paints" Color Research Department, Akzo Nobel Automotive & Aerospace Coatings, Netherlands, Mar. 17, 2015.

* cited by examiner

| Number | Pick-up angle in air | Illumination angle in air | Flake orientation angle in medium |
|---|---|---|---|
| 1 | 15° | -60° | -11.8° |
| 2 | 15° | -30° | -4.5° |
| 3 | 15° | -20° | -1.5° |
| 4 | 15° | 0° | 4.7° |
| 5 | 15° | 30° | 13.8° |
| 6 | 15° | 65° | 22.0° |

SPARKLE MEASUREMENT

BACKGROUND

1. Technical Field

The invention relates to a device for radiometrically gauging the surface of a measurement object that includes effect pigments or flakes embedded in a substrate material.

2. Background Art

Surface coatings comprising embedded flake-shaped effect pigments (flakes) are known to produce a sparkle effect—see for example the reference documents Wissling 2006 and Pfaff 2009. Flake-like effect pigments act as tiny mirrors in the substrate or medium in which they are embedded and reflect incident light. Sparkles become visible when a coating material containing effect pigments is illuminated with directional light, for example, sunlight or light from a point light source. The corresponding visual effect is a pattern of bright light sources which exhibit a high contrast and are superimposed onto the background hue of the coating material. The visual appearance of the sparkle effect is described in more detail in the reference document Kirchner 2007. The terms "appearance", "flake" and "sparkle" have established themselves generally in the relevant specialist circles.

Depending on the type and size of the effect pigments, the sparkles produced by them will have a different brightness and colour distribution. The sparkles of pure-aluminium-based flakes, for example, are perceived as (chromatically) neutral, while other special effect pigments such as, for example, Xirallic Crystal Silver (a trademark of the company Merck KGaA) produce a sparkle pattern which exhibits a broader colour distribution.

Sparkles represent a location-dependent appearance phenomenon which requires (digital) image data of the material surface in order to be characterised. The present invention deals generally with capturing and/or measuring such image data and with the measuring means required for this purpose. More specifically, the invention deals with measurement-technological preconditions and methods for radiometrically gauging sparkles in an image.

One basic aim of every measurement device of the generic type is to capture measurement data which match the appearance of the measurement object, i.e., its visual perception. A visual assessment is typically made under defined observation conditions which include the type of light, illumination intensity, sample size, viewing and illumination geometry and the viewing distance from the sample. Favourable preconditions for a high correlation between the visual appearance and the visualisation of measurement-technological results are achieved if the measurement geometry used and the fundamental measuring technique correspond as far as possible to the observation conditions.

Favourable observation conditions for an accurate appearance assessment require a sample to be illuminated with a sufficient illumination intensity, such that the eye is accommodated and the pupil diameter is typically smaller than 4 mm. Typical observation distances between the eye and the sample are in the range of 250 to 500 mm. The aperture angle of the eye and of the light source are important parameters. They regulate the contrast, number, density and chromaticity of the sparkles which can be visually perceived.

Against this background, it is an object of the invention to provide a device for radiometrically gauging the surface of a measurement object, which is suitable for measuring sparkles and which is optimised in measurement-technological terms for this purpose, wherein the measurement device is in particular intended to be able to provide measurement data which, when visualised, match the visual perception of an observer. Another aim of the invention is to capture device-independent and technology-independent calibrated multispectral measurement data which can be used as a basis for calculating texture scales and for data exchange and communication.

SUMMARY

The present invention advantageously provides a measurement device for radiometrically gauging the surface of a measurement object comprising effect pigments or flakes embedded in a substrate material that includes: (i) at least one measurement array featuring an illumination array and a pick-up array; and (ii) a processor for controlling the illumination array and the pick-up array and for processing measurement signals produced by the pick-up array and for providing processed image data. The illumination array comprises at least one light source and is embodied to expose a region of the measurement object to illumination light at an illumination angle and an illumination aperture angle. The pick-up array comprises a photoelectric image sensor and is embodied to capture measurement light, reflected by the measurement object, at a pick-up angle and a pick-up aperture angle and to direct it onto the image sensor. The illumination array is embodied to produce illumination light in multiple spectral ranges and/or the pick-up array is embodied to split captured measurement light into multiple spectral ranges, such that the image sensor produces multispectral image data. The illumination aperture angle of the illumination array and/or the pick-up aperture angle of the pick-up array is/are greater than the angular variation caused by the material dispersion over the spectral measurement range of the light reflected by an effect pigment or flake embedded in the substrate material.

Dimensioning the illumination aperture angle and the pick-up aperture angle in this way improves the measurement device with respect to its suitability for gauging sparkles, in as much as that this enables it in measurement-technological terms to accurately measure the colour or more generally the multispectral properties of the sparkles and to optimise the detected sparkle density.

The illumination aperture angle of the illumination array and the pick-up aperture angle of the pick-up array advantageously differ by a factor of 2 to 10, wherein the larger of the two aperture angles is at least ±2.5°. The factor by which the illumination aperture angle of the illumination array and the pick-up aperture angle of the pick-up array differ is preferably 4 to 7 and in particular about 5. The pick-up aperture angle is most particularly preferably at least ±0.5° and at most ±1.0°, and the illumination aperture angle is most particularly preferably at least ±2.5°. These ratios of the pick-up aperture angle and the illumination aperture angle enable in measurement-technological terms a favourable colour or multispectral measurement accuracy to be achieved for the sparkles. In addition, a sufficiently high number of sparkles are produced, which is important for a favourably reproducible measurement.

In accordance with a particularly advantageous embodiment, the measurement device in accordance with the invention comprises a second measurement array featuring a corresponding illumination array and pick-up array, wherein in the second measurement array, the illumination aperture angle of the illumination array and the pick-up aperture angle of the pick-up array are of substantially the same magnitude and are at least ±0.5°.

Illumination and pick-up aperture angles which are of substantially the same magnitude and which exhibit a value of greater than or equal to 0.5° improve the measurement device with respect to its suitability for gauging sparkles, inasmuch as that this enables in measurement-technological terms a maximum contrast between sparkles and the background of the measurement object.

The two measurement arrays which are configured differently with respect to their illumination and pick-up aperture angles improve the measurement device both with respect to maximising contrast and with respect to accurately measuring the colour or more generally the multispectral properties of the sparkles and of the detected sparkle density and therefore make it particularly suitable for radiometrically gauging sparkles.

The substantially identical illumination and pick-up aperture angles are preferably in the range of 0.5° to 3.0°.

The substantially identical illumination and pick-up aperture angles expediently differ by not more than 30%, preferably not more than 20%, most particularly preferably not more than 10%.

The pick-up aperture angle is then advantageously at least ±0.5° and at most ±1.0°.

In accordance with a particularly advantageous embodiment of the invention, the measurement device comprises a measurement array featuring two illumination arrays and a common pick-up array, wherein the illumination aperture angle of one illumination array is of substantially the same magnitude as the pick-up aperture angle of the pick-up array and is at least ±0.5° and wherein the illumination aperture angle of the other illumination array is greater, by a factor of 2 to 10, than the pick-up aperture angle of the pick-up array and is at least ±2.5°.

This embodiment improves the suitability of the measurement device for measuring sparkles, both with respect to accurately measuring the colour of the sparkles and with respect to maximising contrast, in a particularly simple way using one measurement array.

In accordance with another advantageous embodiment of the invention, the illumination array and/or the pick-up array comprises means for adjusting the illumination aperture angle and/or the pick-up aperture angle. This configuration enables the same arrays to be used in order to be able to take measurements at different aperture angles (for example with respect to optimised colour measurement accuracy and with respect to optimised contrast) in a sequential measuring process.

In accordance with another particularly advantageous embodiment of the invention, the processor is embodied to correct the measured multispectral image data, such that each wavelength range has a uniform point spread function over the entire measurement field, and each image pixel of a sparkle image contains the radiometrically correct multispectral information. Displaying the multispectral image data on a digital display (for example, a monitor) then provides a digital representation of the sparkles which corresponds to how a human observer would perceive the spectral properties of the sparkles.

In order to achieve optimum compatibility between the visualised image data and/or the values derived from them and the visual perception of an observer, the spatial resolution of the multispectral image data is equal or superior to the resolution limit of the human eye.

The processor is expediently embodied to determine the image pixels which belong to an image of a sparkle and to determine the colour and brightness properties of the sparkle from the multispectral measurement values of these image pixels.

The device is advantageously embodied to produce different multispectral image data for favourable sparkle colour measurement accuracy on the one hand and high sparkle contrast on the other.

Additional advantageous features, functions and benefits of the disclosed invention will be apparent from the description which follows, particularly when read in conjunction with the accompanying figures.

BRIEF DESCRIPTION OF THE FIGURES

In the following description, the invention is described in more detail on the basis of the drawings, which show.

DESCRIPTION OF EXEMPLARY EMBODIMENTS

The following rule applies to the description of the figures below: wherever individual reference signs are not entered in a figure, reference is made in this respect to the other figures and the corresponding parts of the description. Conversely, with respect to elements of a figure which are not explicitly described, reference is made to the corresponding parts of the description relating to other figures.

Figure 1:
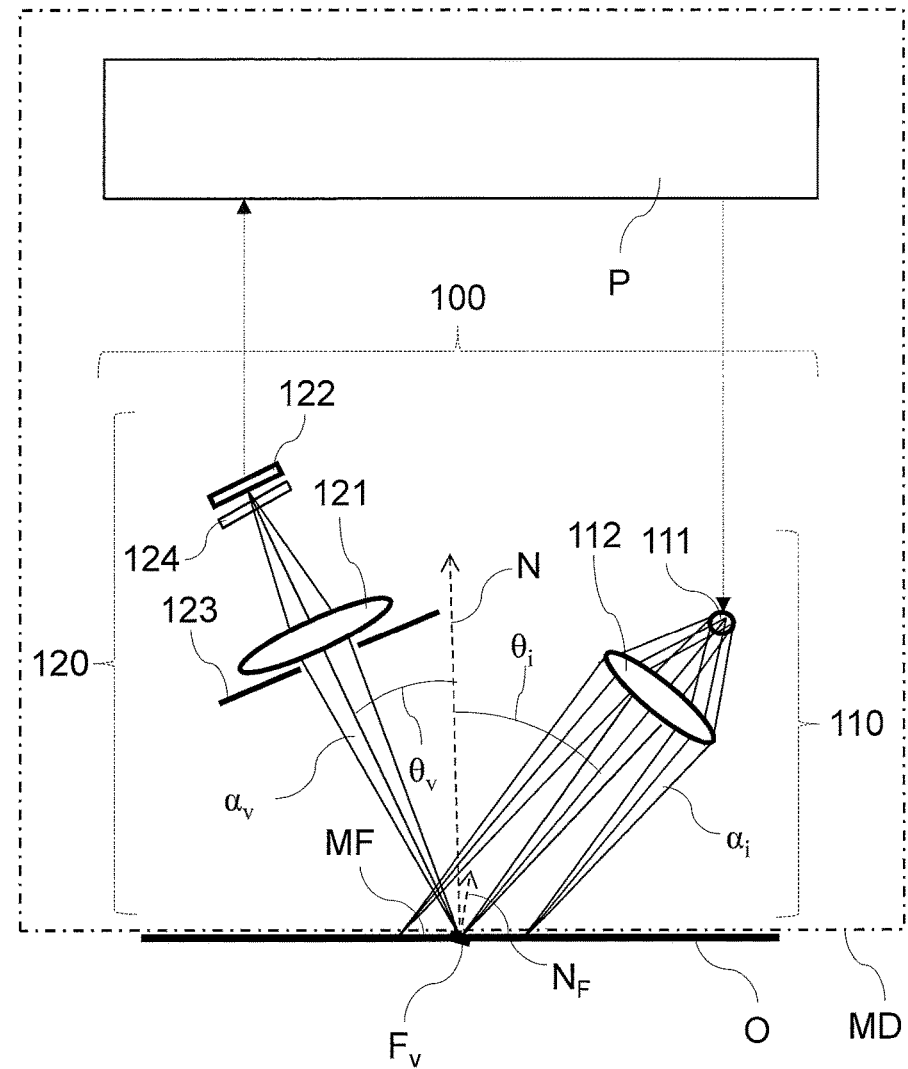
FIG. 1 a schematic representation of the essential arrangement of an example embodiment of the measurement device in accordance with the invention.

In accordance with the representation in FIG. 1, the measurement device in accordance with the invention—which is indicated as a whole by MD—comprises a measurement array 100 featuring an illumination array 110 and a pick-up array 120, as well as a processor P.

The illumination array 110 comprises at least one light source 111 and illumination optics 112 and is embodied to expose a region or measurement spot MF on the surface of a measurement object O to illumination light, namely at an illumination angle $\theta_i$ in relation to a device normal N which (when the measurement device is correctly positioned) coincides with the normal onto the surface of the measurement object O. The illumination array 110 and/or its illumination optics 112 comprise(s) an aperture, wherein the illumination aperture angle of the illumination array 110 is indicated by $\alpha_i$. The aperture angle $\alpha_i$ is to be understood, as is generally typical, to be half of the angular extent of the illumination light distribution in air.

The pick-up array 120 comprises pick-up optics (a lens) 121, a photoelectric image sensor 122 exhibiting a two-dimensional pixel structure, an aperture diaphragm 123 and a set of colour filters 124. The pick-up array 120 is embodied to receive measurement light, reflected by the illuminated surface region (measurement spot) of the measurement object O, at a pick-up angle $\theta_v$ relative to the device normal N and to direct it onto the image sensor 122 by means of the pick-up optics 121. The pick-up array 120 and/or its pick-up optics 121 comprise(s) an aperture, wherein the pick-up aperture angle of the pick-up array 120 is indicated by $\alpha_v$. The aperture angle $\alpha_v$ is to be understood to be half of the angular extent of the captured measurement light.

The pick-up optics 121 are advantageously diffraction-limited or almost diffraction-limited over the entire wavelength range of interest and also have favourable colour correction over the entire image field. Lenses and/or optical systems which meet these requirements are known in their own right. Very high imaging quality is required in order for the measurement device in accordance with the invention to be capable of analysing spectral properties of point light sources and/or sparkles at the resolution limit of the optical imaging system.

The colour filters 124 are configured for multiple different spectral and/or wavelength ranges and can be selectively introduced into the pick-up beam path, for example by means of a rotating filter wheel. The image sensor 122 produces image data which represent, in a digital form, the recorded and/or gauged surface region of the measurement object O, namely for each of the spectral ranges defined by the colour filters 124 (colour channels). The image data produced by the image sensor 122 therefore represent, to a certain extent, colour separations of the recorded surface region of the measurement object O.

The number of colour filters 124 and therefore the number of colour separations and/or colour channels can range from 3 to 40 or more. Three colour filters for the spectral ranges red, green and blue correspond to classic colour measurement; at 20 or more colour channels, a set of spectral measurement data is in practice provided for each pixel. Gauging in three or preferably more wavelength ranges (colour channels) is referred to here and in the following as multispectral.

The image sensor 122 is controlled by the processor P and provides it with the (multispectral) image data to be processed. The processor P also controls the light source(s) 111 of the illumination array 110.

Instead of separate colour filters 124, corresponding colour filters can also be embodied such that they are already integrated in the image sensor 122, i.e. the image sensor 122 can be embodied as a digital RGB colour camera, or as a digital multispectral camera comprising more than three filter channels, by means of structured filters in front of each pixel, wherein the colour camera can also contain multiple image sensors which exhibit different spectral characteristics. The light-sensitive elements (photoreceptors) of the colour camera which exhibit different spectral properties can also be integrated vertically. Monochromators and spectrometers can also be used. Using a monochromator in the illumination array, it is possible to selectively choose a spectral portion of the illumination light. The monochromator in the illumination array thus enables sequential measuring using different illumination spectra. A spectrometer in the pick-up array enables the collected radiation to be spectrally broken down into a number of independent spectral channels which is defined by the spectral resolution of the spectrometer. Different designs of spectrometers for imaging measurement systems are known which enable a sequential measuring method or a simultaneous measuring method.

The colour filters 124 or the colour filters integrated in the image sensor 122 thus represent means for splitting captured measurement light into multiple spectral ranges. Alternatively, it is also possible to embody the illumination array 110 such that it can produce illumination light in multiple spectral ranges. This can for example likewise be achieved by means of colour filters which can be selectively introduced into the illumination beam path or by means of multiple light sources which emit in different spectral ranges, wherein the number of colour channels can likewise be between 3 and about 40 or more.

Instead of colour filters which can be exchanged and/or selectively introduced into the illumination beam path or pick-up beam path, the colour filters can also be embodied such that they can be electrically switched and/or adjusted.

To this extent, the essential design of the measurement device described corresponds to the known appearance measuring devices of this type, such as are for example described in detail in the documents EP 2 728 342 B1 and US 2014/0152990 A1, respectively. How these known appearance measuring devices are physically realised in practice is likewise described in detail in said documents. To this extent, therefore, the person skilled in the art does not require a more detailed description of the essential design of the measurement device or of how it is physically realised in practice.

FIG. 1 shows, purely by way of example, a (virtual) flake $F_v$ which reflects illumination light which is incident at the illumination angle $\theta_i$. A normal onto the (virtual) flake $F_v$ is indicated by $N_F$. The flake $F_v$ is referred to as virtual because the beam paths marked do not take into account and/or show the light refraction in the material in which the flake is embedded.

The sparkles observed at different effect pigments can respectively exhibit characteristic colour distributions. It is therefore of interest to measure, as accurately as possible, the colour or more generally the multispectral properties of the pixels which are associated with sparkles, a sparkle or a spot in the image. This information can for example be used for identifying an effect pigment in a substrate material or for better distinguishing coatings comprising embedded effect pigments which exhibit similar colour or appearance properties.

Measuring, as accurately as possible, the colour or more generally the multispectral properties (measurement values in multiple colour channels and/or spectral ranges) of the image of a point light source, such as a sparkle represents, over a larger wavelength range requires that the optical measurement system fulfils specific conditions. More specifically, the illumination array 110 and the pick-up array 120 and/or the illumination optics 112 and the pick-up optics 121 must be embodied such that the illumination aperture angle $\alpha_i$ on the one hand, and the pick-up aperture angle $\alpha_v$ on the other, fulfil certain conditions.

In an actual coating, the flakes and/or effect pigments are not in the air, but rather embedded into a substrate material and/or medium. This is illustrated in FIG. 2.

Figure 2:
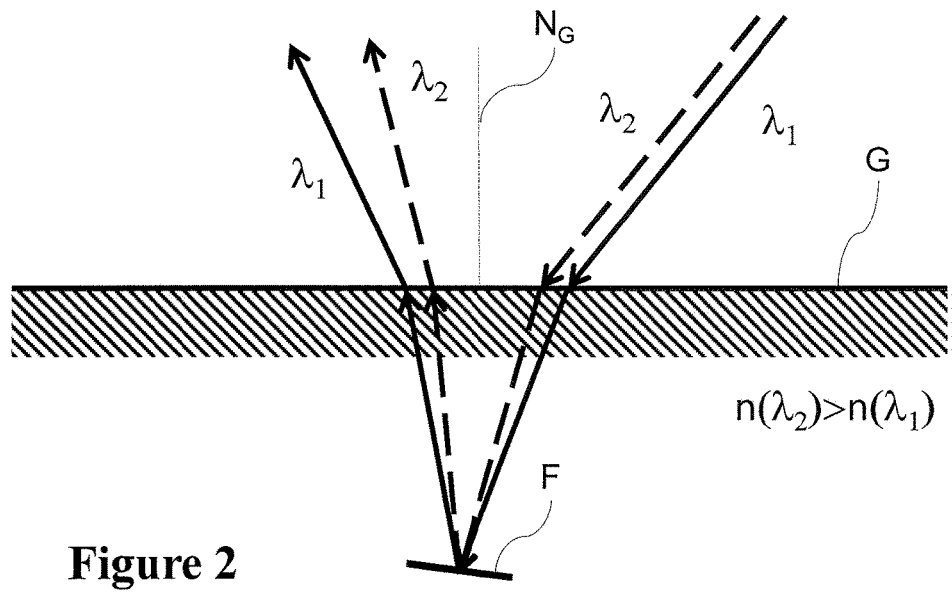
FIG. 2 a sketch describing the light refraction and reflection in a substrate comprising embedded flakes.

FIG. 2 shows two illumination beam paths for different wavelengths $\lambda_1$ and $\lambda_2$, wherein $\lambda_2$ is smaller than $\lambda_1$. The geometrical light beams are refracted at the boundary surface between the air and the medium in accordance with Snell's law. For typical coating materials, the refraction index of smaller wavelengths has a greater value than that of larger wavelengths. Smaller wavelengths are therefore refracted more significantly, i.e. the angular deflection between the two coterminous media is larger. The beam paths marked in FIG. 2 are shown accordingly. In addition, the two beam paths of the different wavelengths are shown such that they are reflected at the same flake F in the medium. It can be seen that the two beam paths exhibit different angles of reflection at the flake F. The reflected beam paths diffuse towards the boundary surface G, where they are again refracted. It can be seen that the beam path of the smaller wavelength $\lambda_2$ is closer to the normal $N_G$ onto the boundary surface G than the beam path of the larger wavelength $\lambda_1$. FIG. 2 also shows a lateral offset between the two beams. A simulation using typical values shows that the lateral offset can be disregarded. The different angles, by contrast, are highly significant for measuring sparkles. The beams reflected by the flake are captured by the pick-up optics 121 and produce an optical image on the camera sensor. The aperture angle $\alpha_v$ of the pick-up array 120 is defined by the aperture diaphragm 123 and determines the angular range of the collected beam paths. Due to the material dispersion, the beam paths of different wavelengths have different angles. The angular offset can lead to an incorrect assessment of the spectral reflection properties of the flake, if the measurement optics of the measurement system cannot compensate for this material-related angular variation.

Figure 3:
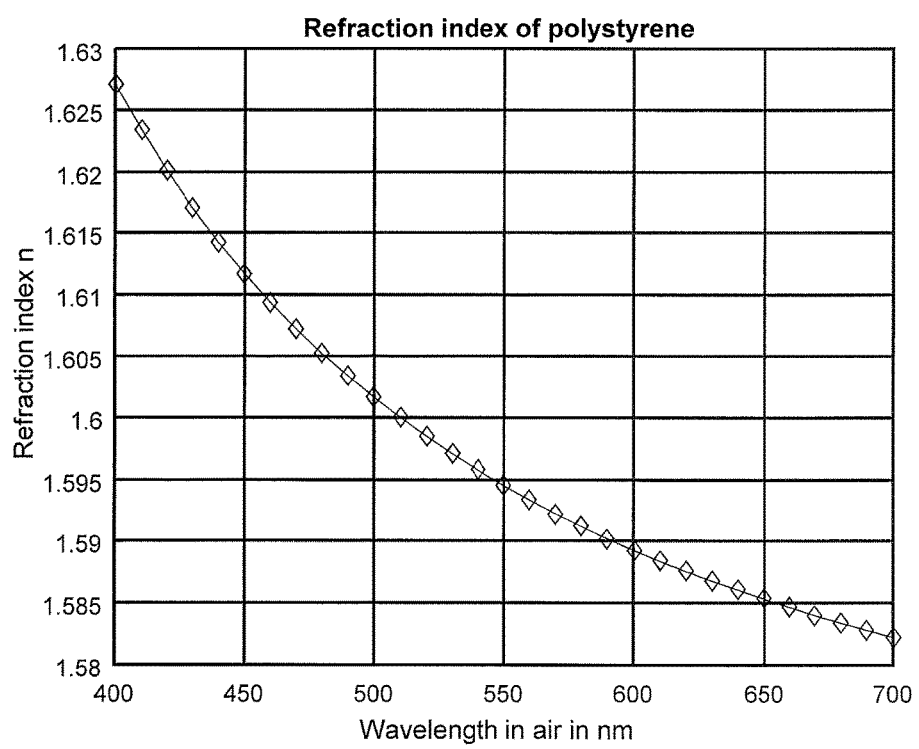
FIG. 3 the distribution of the refraction index n for a transparent plastic material.

The angular variation over the spectral range relevant to measuring is dependent on the measurement geometry and can be calculated if the dispersion of the coating material (medium) is known or has been measured. FIG. 3 shows, as an example, the distribution of the refraction index n for a transparent plastic material (polystyrene) which is also used as a base material for colour-mixing plastics and effect pigments.

Figures 4, 5:
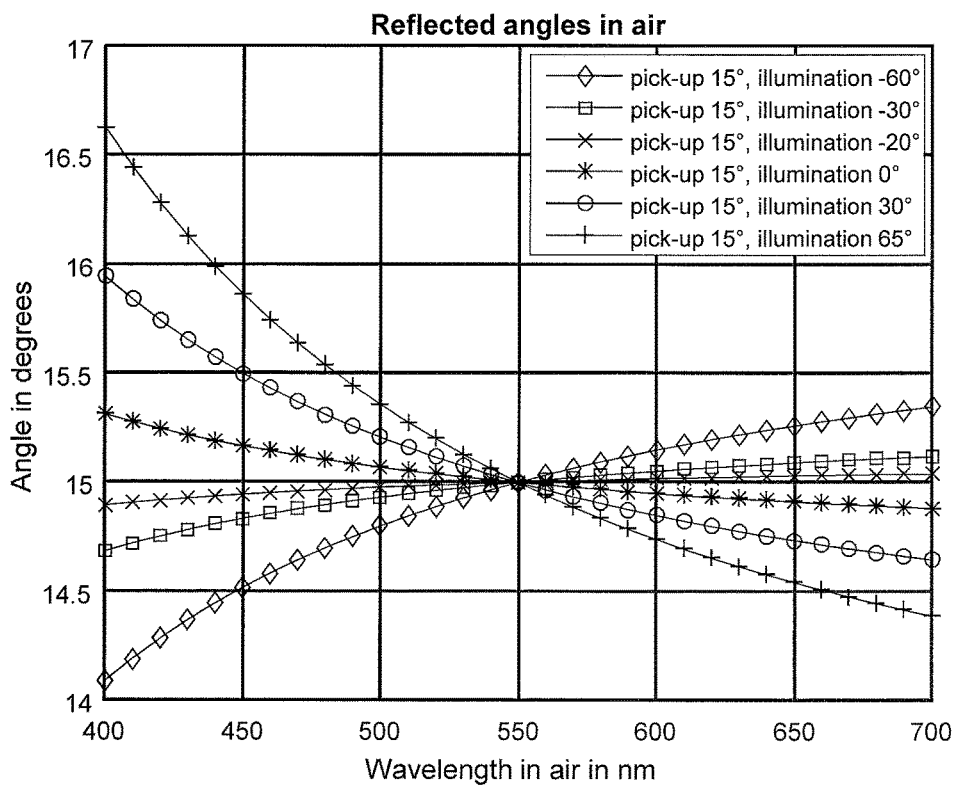
FIG. 4 a table comprising different combinations of illumination and pick-up angles.
FIG. 5 the profile of reflected angles in air for different combinations of illumination and pick-up angles.

FIG. 4 shows a table of different measurement geometries for illumination arrays and pick-up arrays. These angles have been taken from the ASTM E2539 standard. The first two columns contain the pick-up angle of the pick-up array in air and the illumination angle of the illumination array in air. From this angle, it is possible to calculate the orientation angle for a flake in the medium (polystyrene exhibiting a refraction index in accordance with FIG. 3), such that for a mean wavelength of 550 nm, the flake reflects the illumination light into the pick-up angle like a small mirror. The flake orientation angle in the medium is defined relative to the normal $N_G$ onto the boundary surface G (FIG. 2).

For this flake orientation angle, it is then possible to calculate the corresponding reflected angle in air for each wavelength together with the corresponding refraction index of the material for an illumination angle in accordance with the table in FIG. 4. The reflected angles are shown, for all wavelengths between 400 and 700 nm, for the six measurement geometries in FIG. 5. As a result, it is seen that the wavelength-dependent angular variation is dependent on the measurement geometry. The largest angular variation is produced by the measurement geometry No. 6 in FIG. 4 and is about 2° between 400 and 700 nm.

In accordance with a main aspect of the invention, the angular variation caused by the material dispersion can be compensated for if the aperture angle of the illumination array and/or the pick-up array is dimensioned to be greater than the angular variation of the radiation reflected by the flake, as caused by the material dispersion, over the spectral measurement range. This angular variation can be precalculated for the corresponding material dispersions and the measurement geometries used. For appearance measurement devices, a smaller aperture angle in accordance with conditions in the human eye is preferably used in the pick-up array, and the larger aperture angle is realised in the illumination array.

Accurately measuring colour properties and/or multispectral properties requires that the relative spectral properties of the measurement signal remain constant over a certain range of interest of the flake orientation angles. The aperture angle must therefore be configured to be greater than the angular variation produced by the dispersion, in order for this angular condition to apply not only for a flake at an optimum orientation angle but rather for a distribution of flakes at different orientation angles. This enables a more robust evaluation of the colour distribution over the entirety of the measured sparkles in the image. The aperture angle of the smaller pick-up array can be used as the order of magnitude for the additional angular broadening of the aperture angle. As an example: a pick-up aperture angle $\alpha_v$ of the pick-up array of ±0.5° and a dispersion-induced angular broadening over the visible spectral range of 2° result in an illumination aperture angle $\alpha_i$ for the illumination array of greater than ±2.5°.

In practice, measuring the colour or more generally the multispectral properties of the sparkles as accurately as possible is generally enabled by configuring and/or dimensioning the illumination aperture angle $\alpha_i$ of the illumination array 110 and the pick-up aperture angle $\alpha_v$ of the pick-up array 120 in the following way: the illumination aperture angle $\alpha_i$ differs from the pick-up aperture angle $\alpha_v$ by a factor of 2 to 10, preferably by a factor of 4 to 7 and in particular by a factor of about 5, wherein the larger of the two aperture angles $\alpha_i$ and $\alpha_v$ is at least ±2.5°. With regard to signal efficiency, the illumination aperture angle $\alpha_i$ is expediently greater than the pick-up aperture angle $\alpha_v$.

When the measurement device described above is used for radiometrically gauging material surfaces comprising embedded effect pigments, the measured (multispectral) image data also include, in addition to the background hue of the material surface, the sparkles produced by the embedded effect pigments and/or flakes.

It is advantageous for characterising sparkles if the contrast between the sparkles and the background hue of the material in the measured image is as high as possible. When processing the image data in the processor P, a sparkle contrast which is as high as possible improves the discrimination potential of the sparkle signal distribution relative to the background signal in the image data.

In order to achieve a high sparkle contrast in measurement-technological terms, the illumination array 110 and the pick-up array 120 of the measurement array 100 must fulfil certain conditions. More specifically, the illumination array 110 and the pick-up array 120 and/or the illumination optics 112 and the pick-up optics 121 must be embodied such that the illumination aperture angle $\alpha_i$ on the one hand and the pick-up aperture angle $\alpha_v$ on the other fulfil certain conditions.

In accordance with another important aspect of the invention, a maximum contrast is achieved by the fact that the illumination aperture angle $\alpha_i$ of the illumination array 110 and the pick-up aperture angle $\alpha_v$ of the pick-up array 120 are of substantially the same magnitude and are at least ±0.5°, wherein "substantially the same" is to be understood to mean that the two aperture angles $\alpha_i$ and $\alpha_v$ do not differ by more than 30%, preferably not more than 20%, wherein the two aperture angles $\alpha_i$ and $\alpha_v$ can each be in the range of 0.5° to 3.0°. The advantage of aperture enlarging is that it is possible to increase the throughput of light which can be produced, thus enabling the measurement time to be reduced or the signal intensity to be increased.

Configuring the illumination array 110 and the pick-up array 120 such that the above conditions are fulfilled for the two aperture angles $\alpha_i$ and $\alpha_v$ not only leads to optimum contrast but also reduces the dependence of the measurement results on device-specific parameters and facilitates the subsequent evaluation of the image data. In this angular range and under these conditions, it is possible to achieve consistent, comparable measurement results for optimum sparkle contrast.

It follows from the above statements that dimensioning the aperture angles with respect to maximising contrast can differ from dimensioning the aperture angles with regard to optimising the accuracy with which the colour and/or multispectral properties of the sparkles are measured. These two conditions are to a certain extent contradictory and clearly cannot be fulfilled by one and the same measurement array of the type described above. If the measurement device is to be optimised with respect to both sparkle contrast and colour measurement accuracy, it must for example be fitted with two correspondingly optimised measurement arrays for this purpose.

Figure 6:
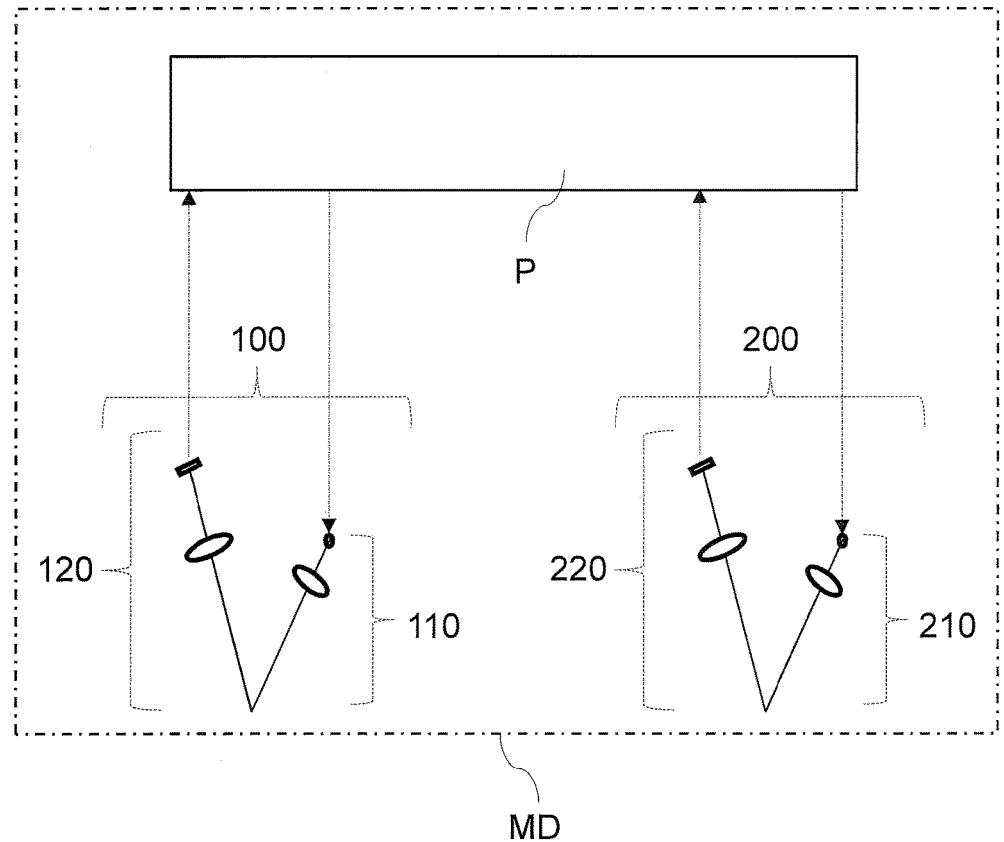
FIGS. 6-8 a significantly simplified schematic representation of the essential arrangement of three other example embodiments of the measurement device in accordance with the invention.

FIG. 6 shows such a measurement device. The measurement device MD here comprises: a first measurement array 100 featuring an illumination array 110 and a pick-up array 120; a second measurement array 200 featuring an illumination array 210 and a pick-up array 220; and a processor P for controlling the two measurement arrays 100 and 200 and for processing the (multispectral) image data produced by them. The measurement arrays 100 and 200 are of fundamentally the same design as the measurement array 100 of FIG. 1, except that the measurement array 100 is optimised with respect to the accuracy with which the colour and/or multispectral properties of the sparkles are measured and the measurement array 200 is optimised with respect to sparkle contrast in accordance with the above descriptions. For the sake of clarity, the two measurement arrays 100 and 200 are shown next to each other in FIG. 6. In reality, however, they are preferably arranged in the measurement device MD such that their illumination arrays 110 and 210, respectively, illuminate one and the same point (measurement spot) on the measurement object, and their pick-up arrays 120 and 220 correspondingly capture measurement light from the same measurement spot.

Figure 7:
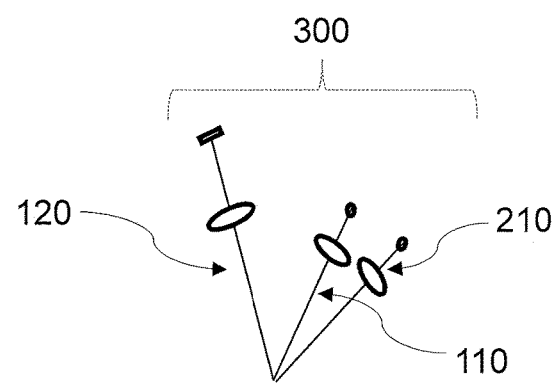

The conditions for the aperture angles on the illumination sides and the pick-up sides can also be fulfilled using a measurement array 300 which is shown schematically in FIG. 7 and comprises two differently configured illumination arrays 110 and 210, exhibiting illumination aperture angles of for example 0.5° and 2.5°, and only one common pick-up array 120 exhibiting a pick-up aperture angle of for example 0.5°.

Figure 8:
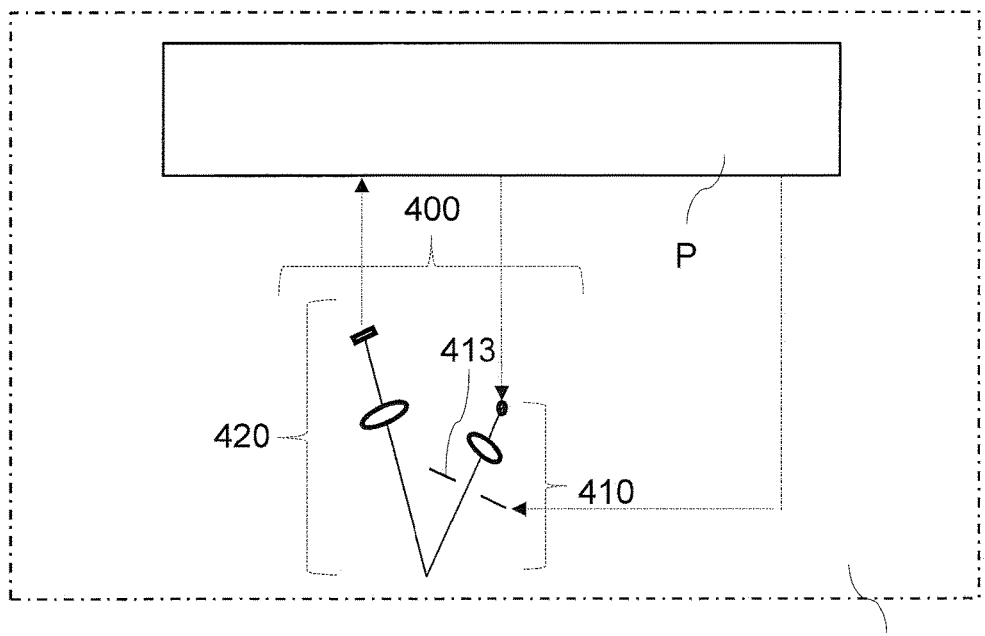

In another variant of the measurement device in accordance with the invention, the illumination aperture angle of the illumination array and/or the pick-up aperture angle of the pick-up array is embodied to be variable. FIG. 8 schematically shows such a measurement device featuring a measurement array 400 which comprises an illumination array 410 and a pick-up array 420. The illumination array 410 and the pick-up array 420 are of substantially the same design as the corresponding arrays 110 and 120 in the example embodiment of FIG. 1. Additionally, a mechanical iris diaphragm 413 which exhibits a variable diameter and can be adjusted by the processor P is arranged in the beam path of the illumination array 410. Such a variable diaphragm can alternatively or additionally also be arranged as an aperture stop diaphragm in the beam path of the pick-up array 420. This configuration enables the same arrays to be used in order to be able to take measurements at different aperture angles in a sequential measuring process, in order for example to switch from colour-optimised measuring to contrast-optimised measuring and vice versa.

The measurement device in accordance with the invention can in principle be fitted with one illumination array or with multiple illumination arrays exhibiting different illumination angles. Similarly, the measurement device can be fitted with one pick-up array or with multiple pick-up arrays exhibiting different pick-up angles. The illumination and pick-up arrays can be positioned in a plane ("in-plane") with the device normal or in different planes ("out-of-plane"). It is in principle also possible to realise illumination arrays with no illumination optics and/or pick-up arrays with no pick-up optics.

Irrespective of the specific embodiments of the measurement device in accordance with the invention, the image sensor of the pick-up system produces a set of spatially resolved measurement signals for each colour channel, the entirety of which is referred to in the following as (digital) multispectral image data. The multispectral image data are thus resolved spatially in accordance with the pixel structure of the image sensor and resolved spectrally and/or in terms of wavelength ranges in accordance with the colour channels of the measurement array.

In order for the multispectral measurement data of each pixel which lies in the image of a sparkle to be correct and able to be used for spectral evaluation, the optical system and preparation of data must fulfil specific requirements which are described in the following.

The (digital) projection and/or measured spatial signal distribution of the projection of a point light source results in principle in a bell-shaped intensity distribution curve. This behaviour is known by the term "point spread". The so-called "point spread function" (referred to below as PSF for short) is described in the literature. The shape of the PSF is dependent on the optical imaging system. The so-called "airy function" is a closed shape of the point spread function produced by a diffraction-limited lens having a circular aperture boundary.

One peculiarity of imaging point light sources by means of an optical system is that the PSF is wavelength-dependent. This means that the point spread functions are different for each colour channel in the measurement device described above.

Figure 9:
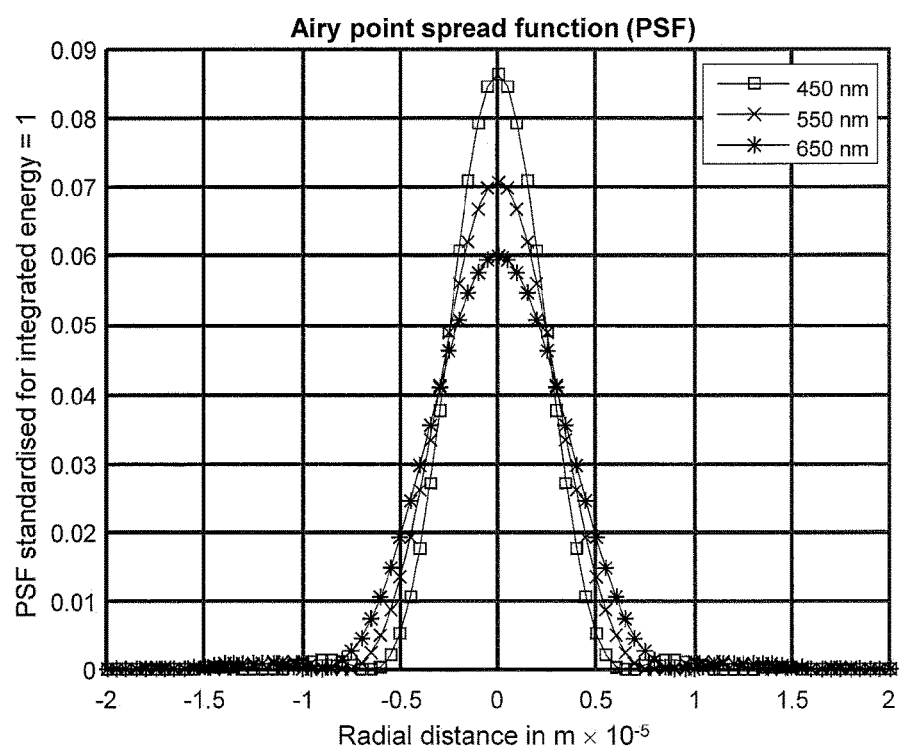
FIG. 9 a diagram of typical point spread functions (PSFs) for different wavelengths.

FIG. 9 shows three typical PSFs (section in one spatial dimension) for three different wavelengths 450 nm, 550 nm and 650 nm. The X-axis indicates the radial distance from the middle of the point; the Y-axis indicates the corresponding standardised intensity values. The standardisation relates to the integral intensity/energy in two dimensions.

Flakes can be smaller in size than the resolution limit of the lens in the object space. In this case, the produced sparkles in the image behave in a similar way to point light sources. The spatial intensity distribution of the sparkle image can in this case be described by the optical PSF of the imaging system. In accordance with FIG. 9, the projection of a sparkle then has a more significant peak in the centre for the colour channels exhibiting shorter wavelengths. This behaviour is caused by the smaller spatial extent of the PSF for the shorter wavelength ranges. This means that if the images ("colour separations") of all the colour channels are recombined into a composite image data array, the distribution of the pixel values within a sparkle is heterogeneous. In the case of an RGB image capture system, white sparkles would show a high-intensity blue spot in the centre and a lower-intensity red ring at the periphery of the sparkle image. This "spectral" heterogeneity across the pixels which cover the region of the detected sparkle makes image analysis using multispectral image data more difficult. Displaying such multispectral image data on a digital display (for example, a monitor) also produces a digital representation of the sparkles which does not correspond to how a human observer would perceive the spectral properties of the sparkles.

Due to these problems, there is a need for better representation of multispectral image data for characteristic sparkle properties which are determined by the material and not by the measuring technology used.

In accordance with another important aspect of the invention, the processor P is embodied to optimise and/or correct the point spread functions of the pick-up array and/or its optics in the course of processing image data, in the sense that the same (optimised) PSF applies for each pixel and in particular for each colour channel (spectral and/or wavelength range), i.e. the (optimised) PSF exhibits the same shape for each colour channel, wherein the optimised and/or corrected PSFs are not device-dependent or technology-dependent. As a result of this measure, each pixel within a detected sparkle exhibits correct spectral properties, and in addition, the image data of each colour channel have the same spatial resolution. How the PSF is optimised and/or corrected and how the multispectral image data are processed on the basis of the corrected PSF is described further below.

Figure 10:
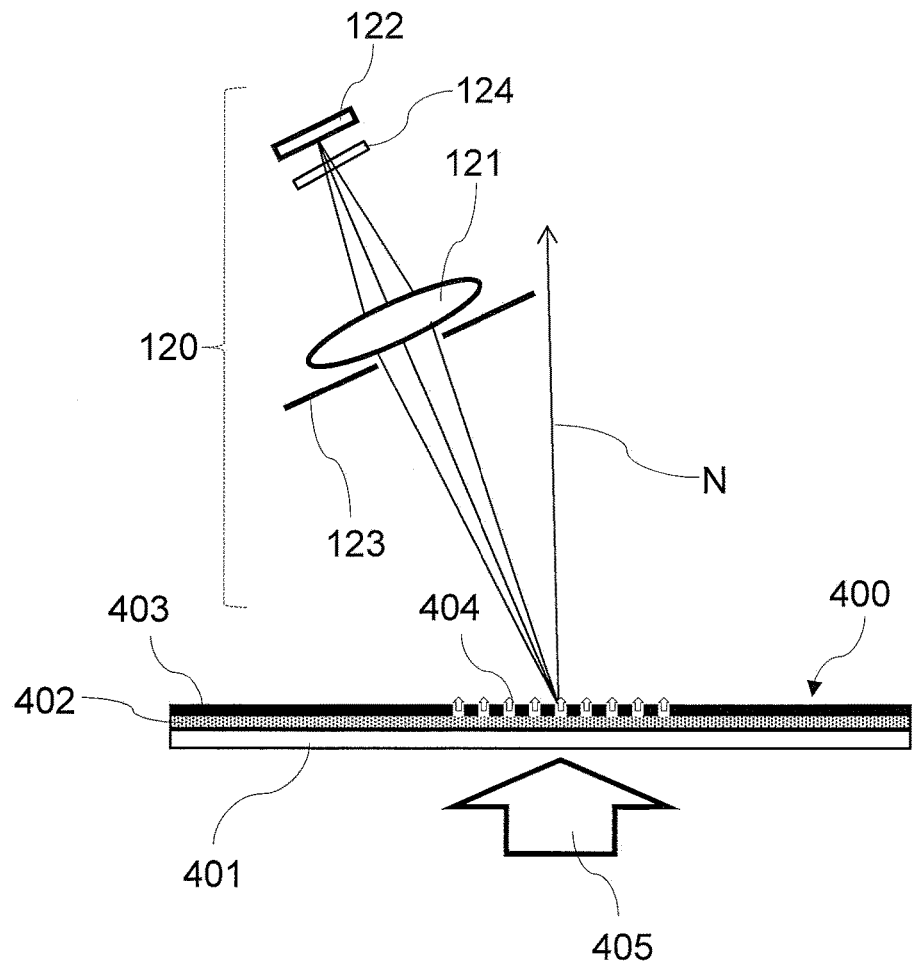
FIG. 10 a schematic representation of an array for measuring point spread functions.

The shape of the PSF for each colour channel of the measurement array can be directly measured using a specific array. FIG. 10 schematically shows how this can be achieved with the aid of a PSF characterisation mask.

For this purpose, the measurement device is placed on a planar PSF characterisation mask 400 which comprises a transparent substrate 401, a diffusely scattering intermediate layer 402 and a shadow mask layer 403 comprising a multitude of fine holes 404. The shadow mask layer can for example be a lithographically produced chromium mask. The intermediate layer can also be omitted and replaced with a diffuse background illumination. The holes 404 are smaller in size than, or of the same order of magnitude as, the resolution of the optical PSF of the pick-up array 120 and/or its pick-up optics 121 in the measurement field plane.

The PSF characterisation mask 400 is illuminated from below (light source 405), such that the fine holes 404 act to a certain extent as point light sources. The PSF characterisation mask 400 is aligned perpendicularly with respect to the device normal N. Of the measurement device itself, only the pick-up array 120 in accordance with FIG. 1 is shown. The illumination array 110 (FIG. 1) is not activated for measuring the PSF; the light source 405 should exhibit similar spectral properties to those of the internal illumination array 110. Alternatively, the shadow mask layer can also be arranged on a diffusely reflecting substrate, wherein it is then illuminated directly by the incident light from the illumination array 110.

Via the pick-up optics 121 and the colour filters 124, the image sensor 122 receives light emitted by the point light sources 404 of the PSF characterisation mask 400 for each colour channel defined by the colour filters 124. The corresponding multispectral image data directly represent the result of convoluting the spatial hole using the point spread functions of the pick-up array 120 and/or its pick-up optics 121 for each colour channel. It should be noted that the PSFs also vary spatially, i.e. a separate PSF applies for each location of the gauged image. The PSF is therefore optimised and/or corrected for each location (pixel), wherein it may be mentioned by way of anticipation that for practical reasons, this is performed exactly for a rough grid of pixels only, and an approximation is made for all intermediate points by interpolation, wherein the PSF characterisation mask 400 and/or its individual holes 404 can serve directly as the grid.

Figure 11:
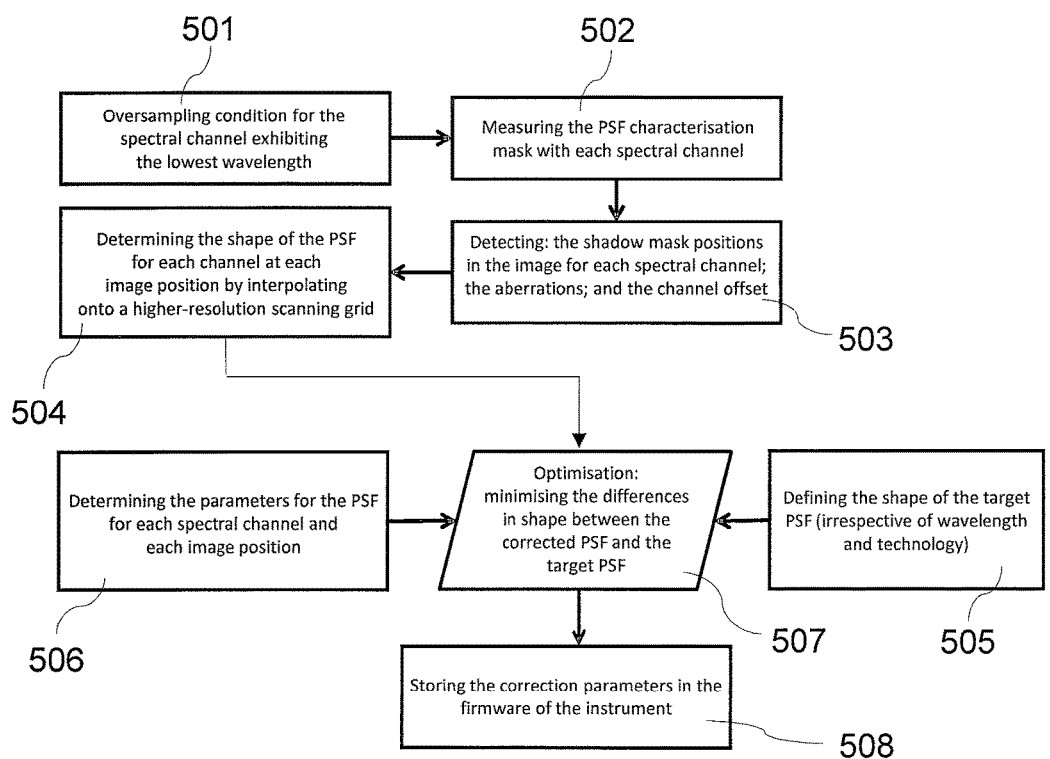
FIG. 11 a block diagram of determining optimised point spread functions.

FIG. 11 describes, on the basis of a block diagram representation, how correction parameters required for optimising the PSF, i.e. achieving a particular uniform shape of the PSF, are formed.

One important precondition is that the image sensor exhibits a sufficiently high spatial resolution in order to be able to scan the measured PSF, to a sufficient level of accuracy, for each colour channel (oversampling, scanning criterion). It has been shown further above on the basis of FIG. 9 that the breadth of the PSF is wavelength-dependent, wherein the smallest breadth results for the colour channel exhibiting the shortest wavelength range. The scanning criterion must be fulfilled for this colour channel. One favourable criterion is that the full breadth of the measured PSF at half of the maximum value (FWHM) is at least twice as large as the scanning interval (pixel distance) of the image sensor. This is symbolised in FIG. 11 by Block 501.

In the next step, symbolised by Block 502, an image ("colour separation") of the PSF characterisation mask 400 is measured for each colour channel.

The position of the point light sources 404 is then detected for each colour channel in the pixel array of the image sensor 122 in Block 503. The position of a point light source is for example characterised by the position of the centre (of area) of the signal distribution of the pixels. Optical aberrations are also measured for each colour channel and stored in the firmware of the measurement device. The position of the point light sources, as measured and/or determined in this way, in the measured image is then compared with the (given and known) position of the point light sources 404 on the PSF characterisation mask 400. The differences in position are characterised for each colour channel and described by a position correction function. This position correction function can for example be a table comprising the measured differences in position over the gauged field and can serve as input information for an interpolating process to determine the correct position of intermediary pixels. Applying this position correction function to each colour channel ensures that the lateral position of each multispectral image is centred onto the same reference position. In particular, the measured centre position of a sparkle point light source is then at the same point for each multispectral image. If the spectral detectors of the image sensor are situated at different points, as for example in a camera filter array, then this spatial deviation (offset) must be measured and corrected as described above.

In the next step (Block 504), the measured image data are initially resampled into a finer scanning grid which is dimensioned arbitrarily and for example exhibits point distances of 25 μm. This resampling is achieved by interpolation, for example in the form of a convolution—see for example Chapter 10.3.3 in the reference document Burger 2009. By correcting the positions and resampling, it is possible to correct deviations in the enlargement between different measurement devices and in the optical system between different measurement devices (chromatic aberrations), in order to obtain comparable geometrical conditions in the object space.

The shape of the PSF is then determined for each colour channel and for each location (positions of the measured light points). The number of multispectral image data values of each point light source is increased for each colour channel by numerically interpolating between the actually measured image data values (pixel values). This oversampling helps to more accurately determine the exact shape of the measured PSF. The shape of the PSF can for example be described by a set of characteristic data, for example by the breadth of the PSF at three different signal levels, for example 80%, 50% and 10% of the maximum value.

Blocks 505 to 507 illustrate the process of correcting the measured PSF. The aim of this correcting process is to alter all the measured PSFs in such a way that they match, as accurately as possible, the shape of a predetermined, device-independent and technology-independent target PSF. The target PSF (Block 505) is defined such that it is broader than the broadest measured PSF. For a high-quality imaging lens, this will be the PSF which has been measured in the colour channel exhibiting the largest wavelengths. Adapting the PSF to a uniform target PSF enables device-independent and technology-independent image data to be produced.

The shape of the PSF is corrected for each colour channel (and each location) by means of an operation of convoluting the measured image data using a defined, parameterised filter function (Block 506). One example of a filter function has a triangular shape (in one dimension) or conical shape (in two dimensions), wherein the breadth of the base of the triangle or cone represents the parameter of the filter function. The parameter(s) of the filter function is/are then determined in an optimising process (Block 507) such that the shape of the corrected PSF is a best match to the shape of the predetermined target PSF. The degree of matching can be determined on the basis of a similarity function. One (very simple) similarity function and/or simple matching criterion can be the breadths of the corrected PSFs (as compared to the target PSF) at different signal levels. At the end of the optimising process, a correction parameter or set of correction parameters is/are provided for each colour channel and each location, which are then stored in the firmware of the measurement device (Block 508). These correction parameters are then used for processing the multispectral image data measured when gauging sparkles. In this way, it is possible to produce corrected measurement and/or image data for each measurement. In summary, there are two types of correction: locational corrections (chromatic aberration, resampling, detector offset) and adapting the resolution (equal, equivalent PSFs).

Figure 12:
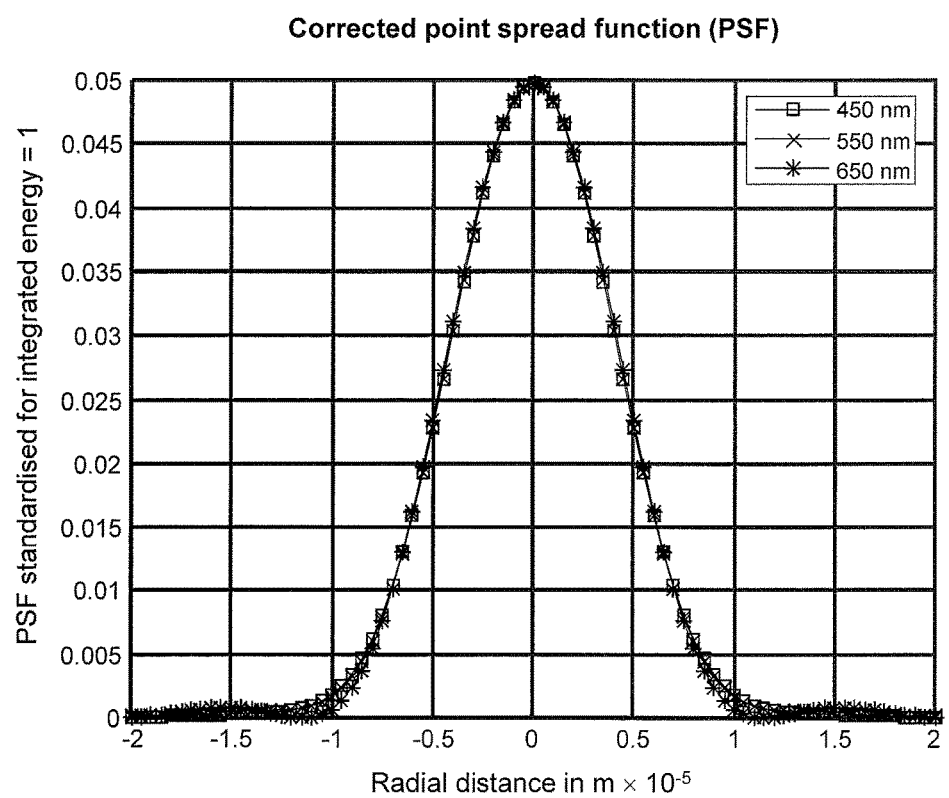
FIG. 12 a diagram of corrected point spread functions.

FIG. 12 shows three typical PSFs (section in one spatial dimension) for three different wavelengths 450 nm, 550 nm and 650 nm which have been obtained using the optimising process just described. The X-axis indicates the radial distance from the middle of the point; the Y-axis indicates the corresponding intensity values which are standardised to the same energy. As can be seen, all three PSFs have the same shape and/or profile (above the 10% value).

Figure 13:
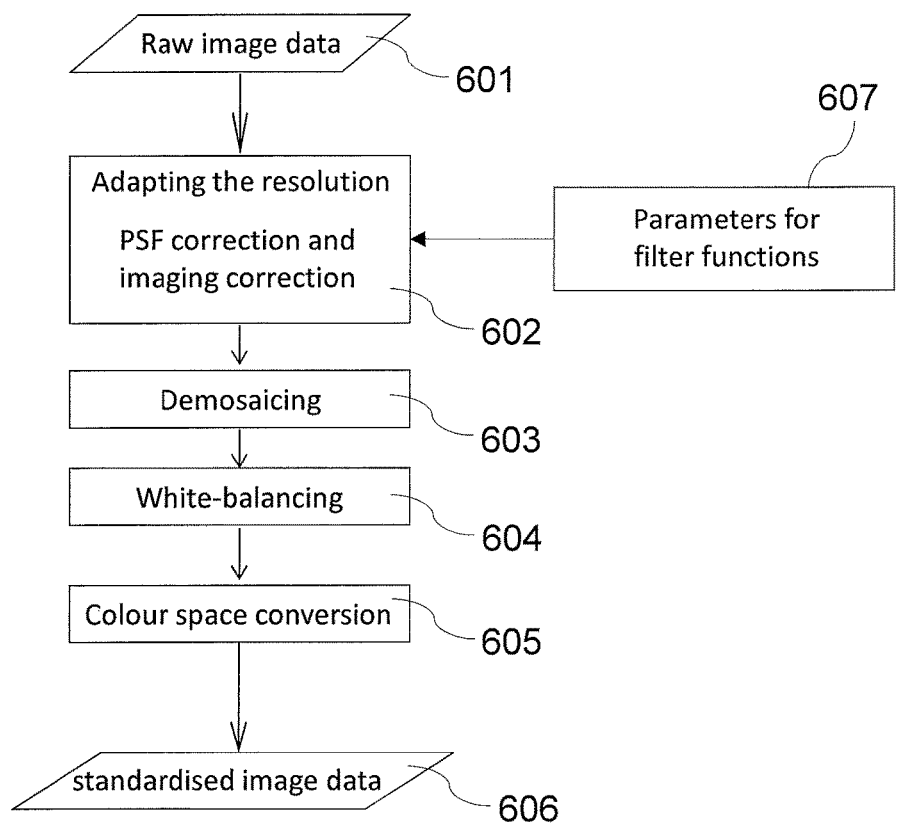
FIG. 13 a block diagram of processing measured image data.

FIG. 13 describes, on the basis of a block diagram representation, how the multispectral image data measured by the image sensor are processed into standardised image data by incorporating the correction to the PSF as mentioned above, and also the locational correction, wherein aside from the PSF correction, the image data are processed in accordance with the processing method described in detail in the documents EP 2 728 342 B 1 and US 2014/0152990 A1, respectively, such that the following description can be limited to the essential points.

The raw multispectral image data measured by the image sensor are represented by Block 601. The optical and spatial resolution of the raw image data is image-sensor-specific. The resolution is adapted in Block 602, wherein the optical and spatial resolution of the image data is adapted such that they correspond to a desired output resolution. The PSF correction and imaging correction mentioned are also made in Block 602, which will be discussed in more detail. So-called demosaicing is then performed in Block 603, in which colour pixels which are separate in terms of location are merged to form one colour pixel. This step can also be omitted, depending on the type of image sensor used. The image data are then white-balanced in Block 604. Finally, the multispectral image data are converted into a colour space, for example the CIE XYZ colour space or sRGB colour space. As a result of all these processing steps, standardised image data are finally provided (Block 606). The resultant image data are device-independent and can be adduced as a basis for calculating other data of interest, for example texture data.

The PSF corrections in Block 602 are performed on the basis of the parameters for the filter function (Block 607) which are stored in the firmware of the measurement device. All operations are performed separately for the image data of each colour channel.

The correction steps described above (convolution, interpolation, imaging corrections, correcting the position of the image sensor) can be computationally very intensive and therefore preferably can be performed by a processor which is specifically embodied and/or programmed for this purpose.

Although the present invention has been described with reference to exemplary embodiments and implementations thereof, the present invention is not limited by or to such exemplary embodiments/implementations. Rather, the present invention may be modified, refined and/or supplemented without departing from the spirit or scope of the present invention.

REFERENCES

Wissling 2006 Wissling, P. (2006). Metallic Effect Pigments: Fundamentals and Applications. Vincentz Network GmbH & Co. KG
Pfaff 2008 Pfaff, G. (2008). Special Effect Pigments: Technical Basics and Applications. Vincentz Network GmbH & Co. KG
Kirchner 2007 Kirchner, E., van den Kieboom, G. J., Njo, L., Super, R., Gottenbos, R. (2007). Observation of Visual Texture of Metallic and Pearlescent Materials. Color Research & Application, 32(4), 256-266
Kirchner 2015 Kirchner, E., van der Lans, I., Perales, E., Martínez-Verdú, F., Campos, J., Ferrero, A. (2015). Visibility of Sparkle in Metallic Paints. JOSA A, 32(5), 921-927
Burger 2009 Wilhelm Burger, Mark J. Burge (2009). Principles of Digital Image Processing: Core Algorithms

The invention claimed is:
1. A device for radiometrically measuring a surface of a measurement object (O) that includes effect pigments or flakes embedded in a substrate material, comprising:
at least one measurement array (100; 200; 300; 400) featuring an illumination array (110; 210; 410) and a pick-up array (120; 220; 420);

a processor (P) configured to control the illumination array (110; 210; 410) and the pick-up array (120; 220; 420) and to process measurement signals produced by the pick-up array (120; 220; 420) and to provide processed image data, and firmware accessible by the processor and in which a plurality of point spread function (PSF) correction parameters are stored, each PSF correction parameter being derived from a corrected device-independent point spread function corresponding to one of a plurality of color channels;

wherein the illumination array (110; 210; 410) comprises at least one light source (111) and is configured to expose a region of the measurement object (O) to illumination light at an illumination angle ($\theta_i$) and an illumination aperture angle ($\alpha_i$), wherein the pick-up array (120; 220; 420) comprises a photoelectric image sensor (122) and is configured to capture measurement light, reflected by the measurement object (O), at a pick-up angle ($\theta_v$) and a pick-up aperture angle ($\alpha_v$) and to direct it onto the image sensor (122), wherein the illumination array (110; 210; 410) is configured to produce illumination light in multiple spectral ranges and/or the pick-up array (120; 220; 420) is configured to split captured measurement light into multiple spectral ranges, such that the image sensor (122) produces multispectral image data corresponding to the plurality of color channels, wherein illumination aperture angle ($\alpha_i$) of the illumination array (110) and/or the pick-up aperture angle ($\alpha_v$) of the pick-up array (120) is/are greater than the angular variation caused by the material dispersion over the spectral measurement range of the light reflected by an effect pigment or flake embedded in the substrate material; and wherein the processed image data is derived from the multispectral image data processed with respective PSF correction parameters.

2. The device according to claim 1, wherein the illumination aperture angle ($\alpha i$) of the illumination array (110) and the pick-up aperture angle ($\alpha_v$) of the pick-up array (120) differ by a factor of 2 to 10, wherein the larger of the two aperture angles ($\alpha_i$, $\alpha_v$) is at least ±2.5°.

3. The device according to claim 2, wherein the factor by which the illumination aperture angle ($\alpha i$) of the illumination array (110) and the pick-up aperture angle ($\alpha_v$) of the pick-up array (120) differ is 4 to 7.

4. The device according to claim 2, wherein the pick-up aperture angle ($\alpha_v$) is at least ±0.5° and at most ±1.0°, and in that the illumination aperture angle ($\alpha_i$) is at least ±2.5°.

5. The device according to claim 1, further comprising a second measurement array (200) featuring a corresponding illumination array (210) and pick-up array (220), wherein in the second measurement array (200), the illumination aperture angle ($\alpha_i$) of the illumination array (210) and the pick-up aperture angle ($\alpha_v$) of the pick-up array (220) are of substantially the same magnitude and are at least +0.5°.

6. The device according to claim 5, wherein the substantially identical illumination and pick-up aperture angles ($\alpha_i$, $\alpha_v$) are in the range of 0.5° to 3.0°.

7. The device according to claim 5, wherein the substantially identical illumination and pick-up aperture angles ($\alpha_i$, $\alpha_v$) differ by not more than 30%.

8. The device according to claim 5, wherein the pick-up aperture angle ($\alpha v$) is at least ±0.5° and at most ±1.0°.

9. The device according to claim 1, wherein the illumination array (410) and/or the pickup array (420) comprises means (413) for adjusting the illumination aperture angle ($\alpha_i$) and/or the pick-up aperture angle ($\alpha_v$).

10. The device according to claim 1, wherein the processor (P) is configured to correct the measured multispectral image data, such that each wavelength range has a uniform point spread function (PSF) over the entire measurement field, and each image pixel of a sparkle image contains the corrected multispectral information.

11. The device according to claim 1, wherein the spatial resolution of the multispectral image data is equal or superior to the resolution limit of the human eye.

12. The device according to claim 1, wherein the processor (P) is embodied to determine the image pixels which belong to an image of a sparkle and to determine the colour and brightness properties of the sparkle from the multispectral measurement values of these image pixels.

13. The device according to any claim 1, wherein the device is embodied to produce different multispectral image data for sparkle colour measurement accuracy on the one hand and high sparkle contrast on the other.

* * * * *